United States Patent
Govari et al.

(10) Patent No.: US 10,682,224 B2
(45) Date of Patent: Jun. 16, 2020

(54) NON-PRESSURIZED AIR BAG IN A BREAST IMPLANT

(71) Applicant: Biosense Webster (Israel) Ltd., Yokneam (IL)

(72) Inventors: Assaf Govari, Haifa (IL); Yehuda Algawi, Binyamina (IL)

(73) Assignee: BIOSENSE WEBSTER (ISRAEL) LTD., Yokneam (IL)

(*) Notice: Subject to any disclaimer, the term of this patent is extended or adjusted under 35 U.S.C. 154(b) by 19 days.

(21) Appl. No.: 15/817,585

(22) Filed: Nov. 20, 2017

(65) Prior Publication Data
US 2019/0151075 A1 May 23, 2019

(51) Int. Cl.
*A61F 2/12* (2006.01)

(52) U.S. Cl.
CPC ........ *A61F 2/12* (2013.01); *A61F 2210/0057* (2013.01); *A61F 2240/001* (2013.01); *A61F 2250/0003* (2013.01)

(58) Field of Classification Search
CPC ................ A61F 2/12; A61F 2210/0057; A61F 2210/0061
See application file for complete search history.

(56) References Cited

U.S. PATENT DOCUMENTS

| | | | | | |
|---|---|---|---|---|---|
| 3,845,507 A | * | 11/1974 | Kirby | ................. | A61F 2/52 623/7 |
| 4,125,117 A | * | 11/1978 | Lee | ................ | A61F 2/52 450/54 |
| 4,298,998 A | * | 11/1981 | Naficy | ................. | A61F 2/12 623/8 |
| 4,426,742 A | * | 1/1984 | Prahl | ................... | A61F 2/52 450/81 |
| 4,605,412 A | * | 8/1986 | LaForest | ................ | A61F 2/12 128/899 |
| 4,790,848 A | * | 12/1988 | Cronin | ................ | A61F 2/12 623/8 |
| 5,383,929 A | * | 1/1995 | Ledergerber | ........... | A61F 2/0077 623/8 |
| 5,496,367 A | * | 3/1996 | Fisher | ................ | A61F 2/12 623/8 |
| 5,534,023 A | * | 7/1996 | Henley | ................ | A61F 2/12 623/7 |

(Continued)

FOREIGN PATENT DOCUMENTS

GB   2388780 A   11/2003

OTHER PUBLICATIONS

International Search Report dated Feb. 11, 2019 from corresponding PCT Application No. PCT/IB2018/058952.

*Primary Examiner* — Seema Mathew
(74) *Attorney, Agent, or Firm* — Eugene L. Szczecina, Jr.

(57) ABSTRACT

An implantable device includes a first sealed flexible shell configured for implantation within a breast of a human subject, an elastic filler material contained within the first sealed flexible shell, a second sealed flexible shell, which is disposed within the elastic filler material inside the first sealed flexible shell and a volume of gas contained within the second sealed flexible shell, such that the volume of the gas is less than a threshold inflation volume required to induce a non-zero strain in the second sealed flexible shell when the device is subject to an external pressure of one atmosphere.

8 Claims, 5 Drawing Sheets

(56) References Cited

U.S. PATENT DOCUMENTS

| | | | | |
|---|---|---|---|---|
| 5,549,671 | A * | 8/1996 | Waybright | A61F 2/12 623/7 |
| 8,080,057 | B2 * | 12/2011 | Kronowitz | A61F 2/12 128/898 |
| 8,205,356 | B2 | 6/2012 | Ellis | |
| 8,398,710 | B2 * | 3/2013 | Forsell | A61F 2/12 623/8 |
| 9,017,403 | B2 * | 4/2015 | Forsell | A61F 2/12 623/8 |
| 9,339,371 | B2 * | 5/2016 | Dvir | A61F 2/12 |
| 9,370,414 | B2 * | 6/2016 | Glicksman | A61F 2/12 |
| 9,399,122 | B2 * | 7/2016 | Mosharrafa | A61F 2/12 |
| 9,486,309 | B2 | 11/2016 | Schuessler | |
| 9,713,524 | B2 * | 7/2017 | Glicksman | A61F 2/12 |
| 10,052,191 | B2 * | 8/2018 | Govrin-Yehudian | A61F 2/12 |
| 10,383,510 | B2 * | 8/2019 | Schutt | A61B 17/00234 |
| 2009/0099656 | A1 * | 4/2009 | Gelda | A61F 2/12 623/8 |
| 2009/0299473 | A1 * | 12/2009 | Govrin-Yehudian | A61F 2/12 623/8 |
| 2009/0326654 | A1 * | 12/2009 | Powell | A61F 2/12 623/8 |
| 2011/0152913 | A1 * | 6/2011 | Jones | A61F 2/12 606/192 |
| 2012/0277860 | A1 * | 11/2012 | Dvir | A61F 2/12 623/11.11 |
| 2016/0256295 | A1 | 9/2016 | Wollnick et al. | |
| 2017/0367809 | A1 * | 12/2017 | Glicksman | A61F 2/12 |

* cited by examiner

NON-PRESSURIZED AIR BAG IN A BREAST IMPLANT

FIELD OF THE INVENTION

The present invention relates generally to medical devices, and particularly to breast implants.

BACKGROUND

A breast implant is either inserted in a human breast or attached on the breast in order to replace tissue that has been medically removed in an operation such as a mastectomy. The purpose of the breast implant is to restore to the breast its initial form, including its tactile feel and weight. A breast implant may also be inserted in a breast to enhance or enlarge the appearance of the breast for cosmetic purposes.

UK Patent Application GB2,388,780 describes an external breast implant of reduced weight, which includes a main body and one or more air sacs.

U.S. Pat. No. 4,125,117 describes a universal breast implant usable as a substitute for either the right or left breast and for patients who have had varying degrees of surgery, scarring, muscle removal and the like, having an upper flap and symmetrical lateral flaps.

U.S. Pat. No. 8,205,356 describes attempts to replicate in footwear, orthotics, and other products the naturally effective anatomical structures like a bare foot that provide superior flexibility, cushioning, and stable support compared to existing products.

U.S. Pat. No. 8,080,057 describes methods for optimal breast reconstruction, including steps for performing a mastectomy that preserves a breast skin envelope.

U.S. Pat. No. 9,399,122 describes methods and systems for a tissue expander, which may function in conjunction with an extended tissue expander, such as an extended tissue expander to be temporarily implanted into a patient to form a pocket for a permanent implant.

SUMMARY

Embodiments of the present invention that are described hereinbelow provide for an improved breast implant.

There is therefore provided, in accordance with an embodiment of the present invention, an implantable device, which includes a first sealed flexible shell configured for implantation within a breast of a human subject, an elastic filler material contained within the first sealed flexible shell, a second sealed flexible shell, which is disposed within the elastic filler material inside the first sealed flexible shell, and a volume of gas contained within the second sealed flexible shell, such that the volume of the gas is less than a threshold inflation volume required to induce a non-zero strain in the second sealed flexible shell when the device is subject to an external pressure of one atmosphere.

In an embodiment the elastic filler material includes silicone gel.

In another embodiment the volume of gas includes a volume of air.

In a further embodiment the volume of the gas comprises 85% of the threshold inflation volume.

There is also provided, in accordance with an embodiment of the present invention, a method for manufacturing an implantable device, the method including providing a first sealed flexible shell configured for implantation within a breast of a human subject, filling the first sealed flexible shell with an elastic filler material, disposing a second sealed flexible shell within the elastic filler material inside the first sealed flexible shell, and inflating the second sealed flexible shell with a volume of gas, such that the volume of the gas is less than a threshold inflation volume required to induce a non-zero strain in the second sealed flexible shell when the device is subject to an external pressure of one atmosphere.

In an embodiment, filling the first sealed flexible shell includes filling it with silicone gel.

In another embodiment, inflating the second sealed flexible shell comprises inflating it with air.

The present invention will be more fully understood from the following detailed description of the embodiments thereof, taken together with the drawings in which:

DETAILED DESCRIPTION OF EMBODIMENTS

Overview

A commonly used breast implant is an implant wherein an elastic filler material, such as silicone gel, is contained in a first sealed flexible shell. However, a breast implant that is completely filled with such a material is relatively heavy, and may cause discomfort to the wearer of the implant.

Embodiments of the present invention provide an implantable device that is used as a breast implant. The device comprises a first sealed flexible shell that is configured for implantation within a breast of a human subject. An elastic filler material is contained within the first flexible shell, and there is a second sealed flexible shell that is disposed within the elastic filler material.

There is a volume of gas within the second sealed shell, and the volume of gas is selected to be less than a threshold inflation volume. The threshold inflation volume is a gas volume that induces a non-zero strain in the second sealed shell then the device is subject to an external pressure of one atmosphere.

Embodiments of the present invention that are described herein address the potential for gas leakage so as to enable the construction of a breast implant equipped with a balloon-like second shell with no appreciable gas leakage over the lifetime of the implant. This enables the construction and fabrication of light-weight and stable breast implants.

The disclosed embodiments reduce any potential gas leakage to below a preset limit by inflating the second shell only partially, as will be detailed below.

System Description

Figure 1:
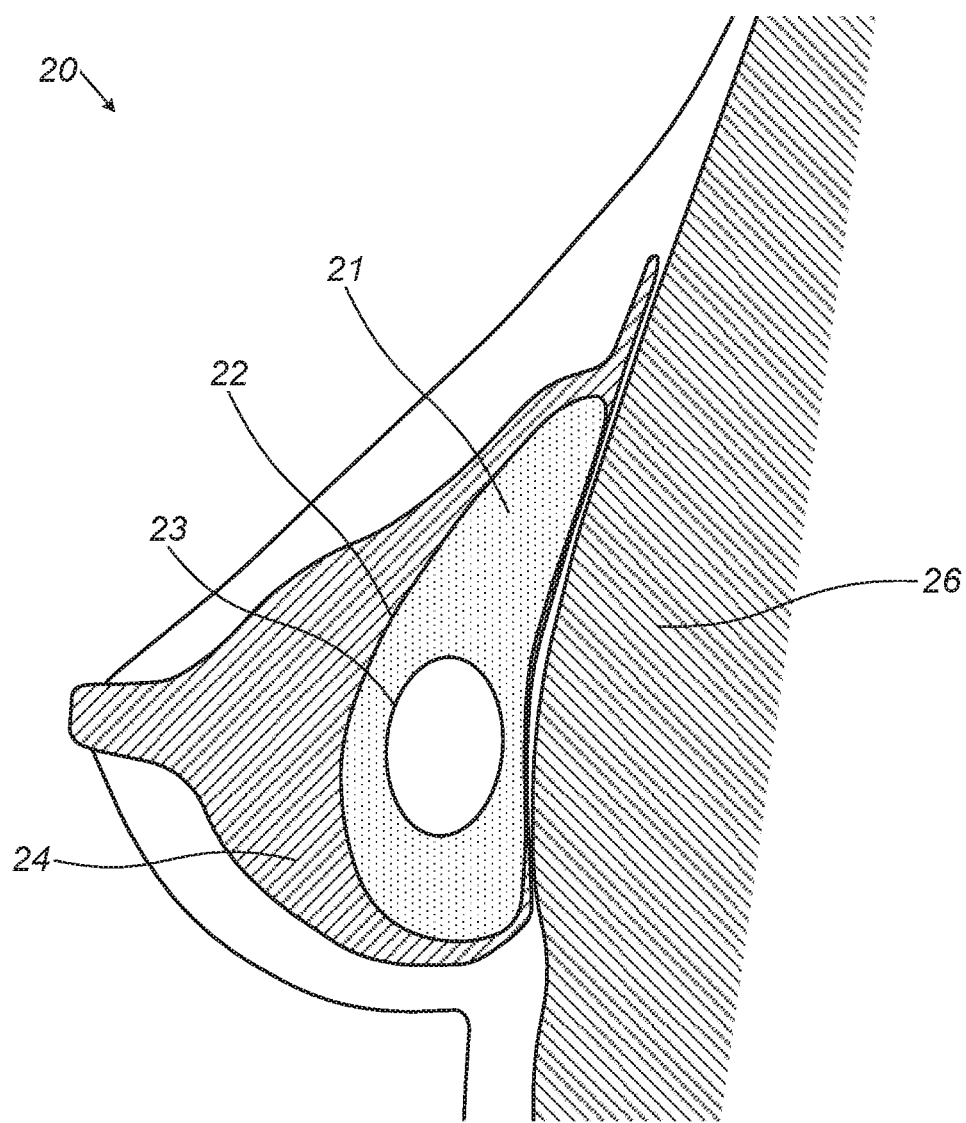
FIG. 1 is a schematic sectional illustration of a human female breast with a breast implant, in accordance with an embodiment of the invention.

FIG. 1 is a schematic sectional illustration of a human female breast 20 with a breast implant 21, in accordance with an embodiment of the present invention. Implant 21 comprises a first shell 22 and a second shell 23, described in more detail below. In the disclosed embodiment, breast implant 21 is positioned as a subglandular implant between breast tissue 24 and a pectoralis major muscle 26. In alternative embodiments, breast implant 21 may be positioned either as a subfascial, subpectoral, or submuscular implant, referring to different positions of the implant relative to pectoralis major muscle 26, as will be understood by those skilled in the art.

Figure 2:
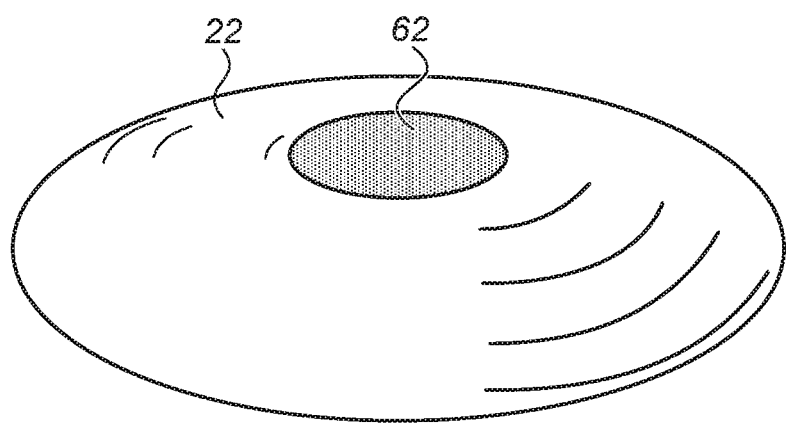
FIG. 2 is a schematic perspective view of a first shell of a breast implant, in accordance with an embodiment of the invention.

FIG. 2 is a schematic perspective view of first shell 22 of breast implant 21, in accordance with an embodiment of the invention. First shell 22 is fabricated by repeatedly dipping a mandrel (not shown) in a silicone solution. The coat of the silicone solution is allowed to solidify between consecutive dips. Once a sufficient thickness of the silicone layer covering the mandrel, typically 0.1 mm, has been reached and the silicone has solidified, the silicone "skin" is peeled off the mandrel. An opening 62 is left in first shell 22 by the stem of the mandrel.

Figure 3:
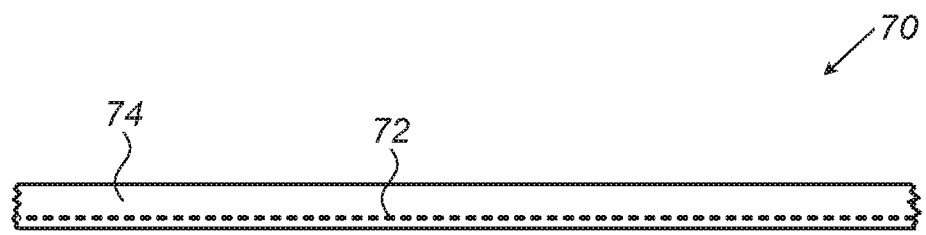
FIG. 3 is a schematic sectional view of polyamide/polyurethane (PA/PU) composite material, in accordance with an embodiment of the invention.

FIG. 3 is a schematic sectional view of a polyamide/polyurethane (PA/PU) composite material 70, in accordance with an embodiment of the invention. PA/PU composite material 70 (or similar flexible and inelastic material) is used for second shell 23. The flexibility of second shell 23 allows the shell to adapt its shape to the changing shape of implant 21 due to e.g. movement of breast 20. The inelasticity of second shell 23 prevents the shell, and thus implant 21, from changing its size in a low-pressure environment, such as an airplane.

Composite material 70 is fabricated by dipping a fine net of PA (polyamide) 72 in liquid PU (polyurethane) 74. The composite is then fed through two parallel rollers to flatten out the sheet.

Figure 4:
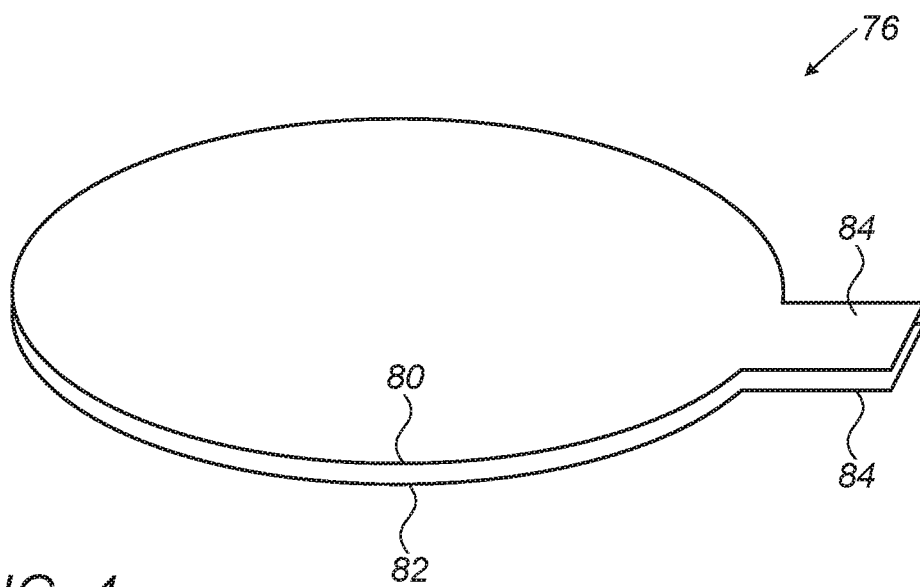
FIG. 4 is a schematic perspective view of cut PA/PU composite material prepared for radio frequency (RF) welding, in accordance with an embodiment of the invention.

FIG. 4 is a schematic perspective view of PA/PU composite material 70 after it has been cut in preparation for radio frequency (RF) welding, in accordance with an embodiment of the invention. Two similarly shaped pieces have been cut out of PA/PU composite material 70, forming an upper composite sheet 80 and a lower composite sheet 82 that together form a second shell preform 76. As described below sheets 80 and 82 are used to form second shell 23, and the shape of sheets 80 and 82 may be circular, square, or any other desired shape for second shell 23. An extension 84 is left on each part to form a fill tube 86 (shown in FIG. 5) after RF welding.

Figure 5:
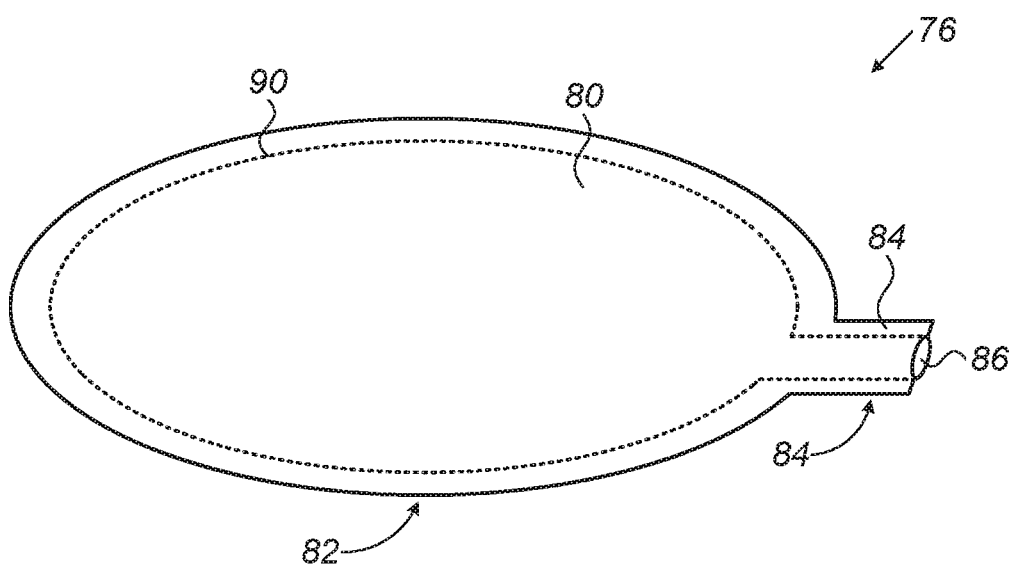
FIG. 5 is a schematic perspective view of a second shell preform after RF welding of two composite sheets, in accordance with an embodiment of the invention.

FIG. 5 is a schematic perspective view of second shell preform 76 after RF welding of upper and lower composite sheets 80 and 82, respectively, in accordance with an embodiment of the invention. Upper and lower composite sheets 80 and 82, respectively, have been RF welded together along a weld line 90 positioned at the perimeters of the sheets. In the process, a fill tube 86 has been formed from extensions 84, to be used for inflating second shell preform 76.

Figure 6:
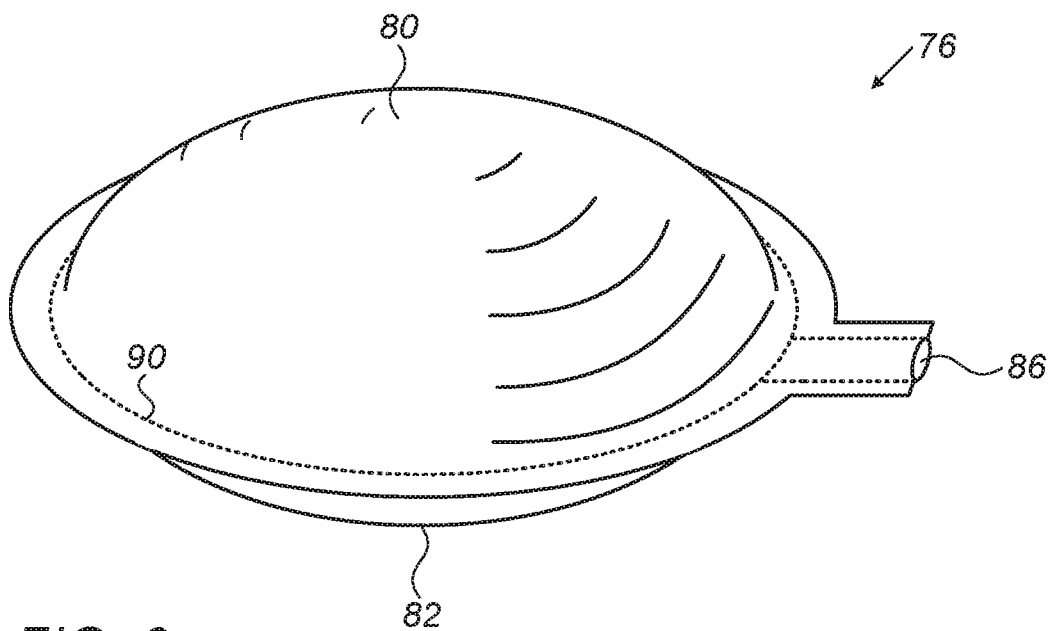
FIG. 6 is a schematic perspective view of a second shell preform after an inflation step, in accordance with an embodiment of the invention.

FIG. 6 is a schematic perspective view of second shell preform 76 after the preform has been partially inflated, in accordance with an embodiment of the invention. Upper and lower composite sheets 80 and 82, respectively, have formed a balloon-like volume due to the partial inflation of second shell preform 76 through fill tube 86.

By partial inflation we mean inflating the second shell with gas to a volume $V<V_{th}$, while the shell is subject to an external pressure of one atmosphere. A threshold inflation volume of the second shell, $V_{th}$, is defined as an inflation volume that would induce a non-zero strain in the shell. The volume of the shell and the volume of the gas are the same when the gas is at a pressure of one atmosphere. A typical value for V is 85% of $V_{th}$. Partial inflation of the second shell (rather than full inflation) reduces the potential diffusion of gas into the elastic filler material of the implant to below a preset limit.

Figure 7:
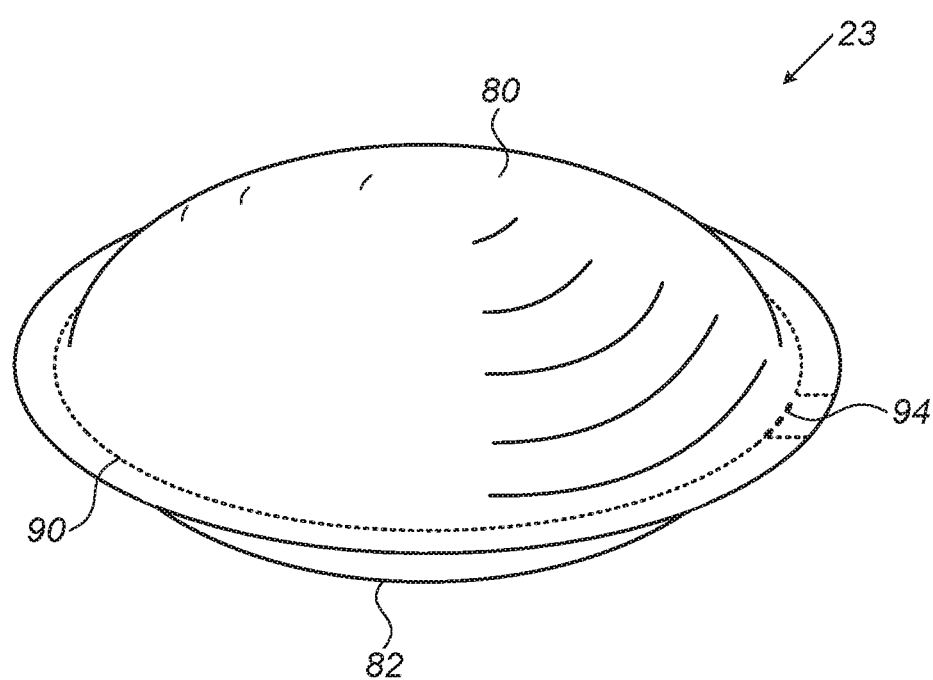
FIG. 7 is a schematic perspective view of a second shell preform after a seal step, in accordance with an embodiment of the invention.

FIG. 7 is a schematic perspective view of completed second shell 23 formed from preform 76, in accordance with an embodiment of the invention. Initial RF weld 90 has been completed with a sealing RF weld 94, thus completely sealing-off the gas volume between upper and lower composite sheets 80 and 82, respectively. In addition, the part of fill tube 86 outside the edge of second shell preform 76 has been cut off.

Figure 8:
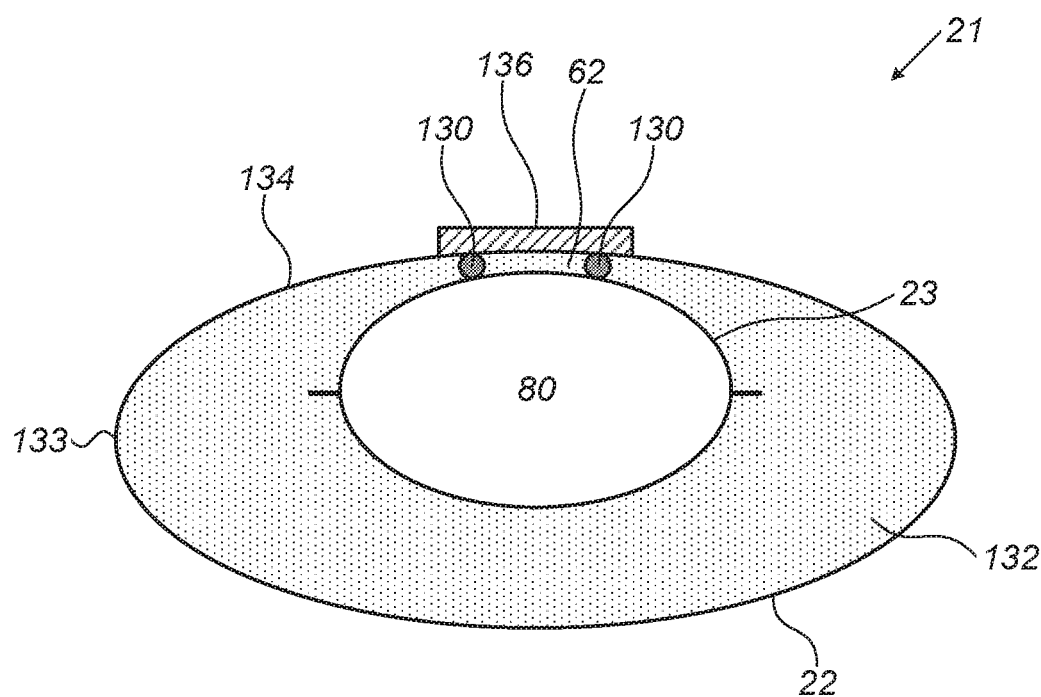
FIG. 8 is a schematic sectional view of a completed breast implant, in accordance with an embodiment of the invention.

FIG. 8 is a schematic sectional view of completed breast implant 21, in accordance with an embodiment of the invention. Completed second shell 23 (FIG. 7) has been inserted into first shell 22 (FIG. 2) through opening 62. Second shell 23 is further secured in place by a ring of cement 130, which attaches the second shell to first shell 22. Cement 130 also closes off the inside of first shell 22, thus enabling the subsequent filling of the first shell without leakage of the fill material, as will be described below. Elements 132, 133, 134, and 136 are described further below.

Figure 9:
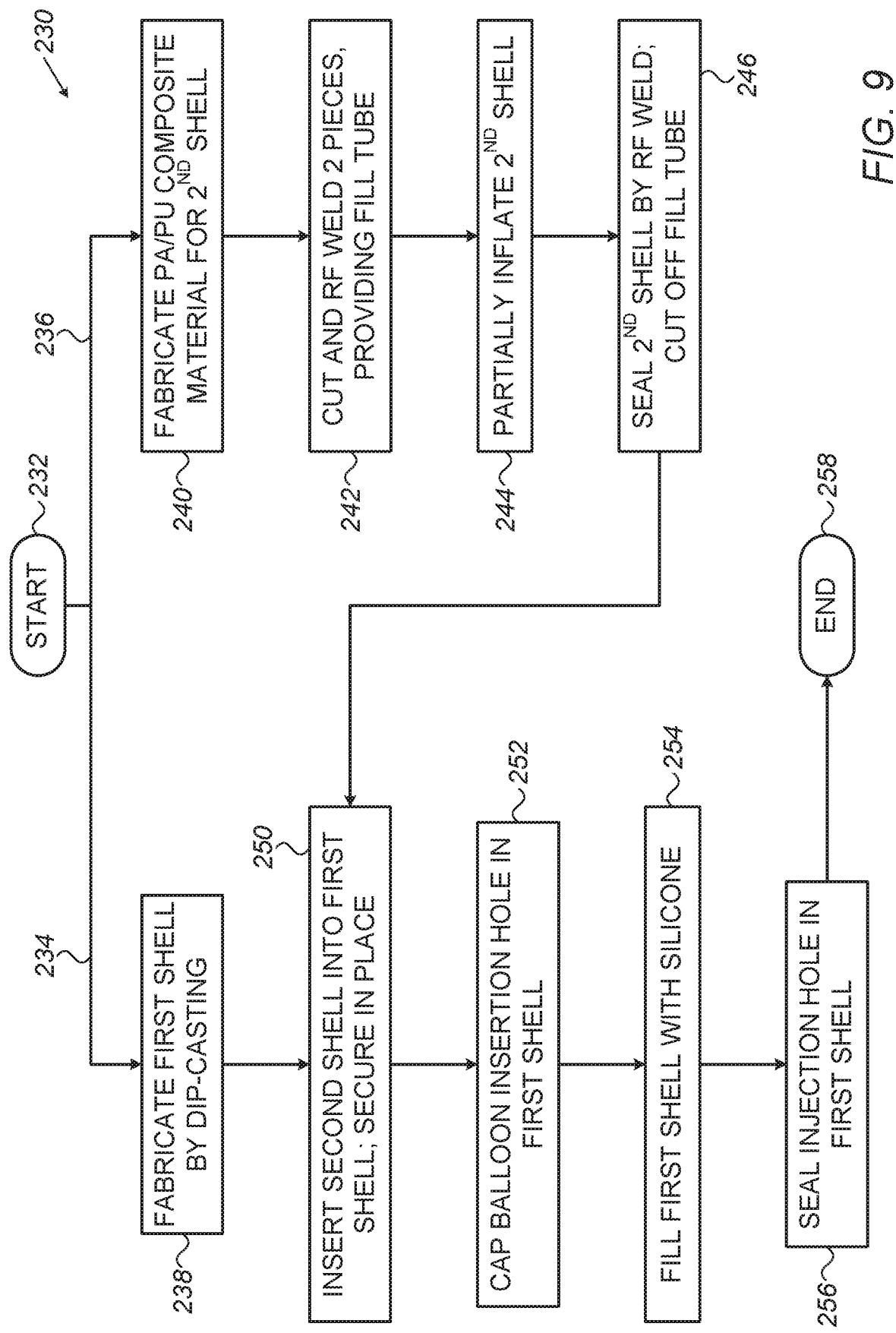
FIG. 9 is a flowchart that schematically illustrates a method for fabricating a breast implant, in accordance with an embodiment of the invention.

FIG. 9 is a flowchart 230 that schematically illustrates a method for fabricating breast implant 21, in accordance with an embodiment of the invention. The method splits into two paths 234 and 236 from a start step 232. Path 234 leads to a first shell fabricating step 238, which comprises the fabrication of first shell 22 by dip-casting as described above with reference to FIG. 2. Path 236 leads to steps 240-246 for fabricating second shell 23. In a material fabrication step 240 composite material 70 for second shell 23 is fabricated as described above with reference to FIG. 3. In a cut and weld step 242, two pieces 80 and 82 of composite material 70 are cut to shape and attached to each other to form second shell preform 76 with fill tube 86 as described above with reference to FIGS. 4-5. In a partial inflation step 244 second shell preform 76 is partially inflated with gas as described above with reference to FIG. 6. In a seal step 246 partially inflated second shell preform 76 is sealed with an RF weld and fill tube 86 is cut off as described above with reference to FIG. 7. The result of seal step 246 is completed second shell 23.

Step 238 and steps 240-246 may be implemented serially or in parallel. These steps converge in a second shell insertion step 250, where completed second shell 23 is inserted and secured in first shell 22 as described above with reference to FIG. 8. Further referencing FIG. 8, in a cap step 252 a cap 136 of the same material as first shell 22 is used to close opening 62. The use of cap 136, in addition to cement 130, further secures implant 21 against leaks of elastic filler material 132.

In an implant fill step 254 first shell 22 is filled with an elastic filler material 132 using a syringe (not shown) through a shell wall 133 at a location 134, until a predetermined volume of material has been injected. A typical volume of breast implant 21 is 800 cc. If second shell 23 is not inserted into the first shell, the entire 800 cc volume would be filled with silicone, weighing approximately 800 g. The volume of second shell is typically 30-40% of the total volume of breast implant 21, leading to a reduction of the injected silicone by 30-40% of the volume of 800 cc, which in turn reduces the weight of the implant by 30-40% of the weight of 800 g.

Elastic filler material 132 typically comprises a 2-component silicone gel. The silicone gel is a viscose liquid while being injected through the syringe. Before the silicone gel is injected into first shell 22, air bubbles are removed from the gel under vacuum.

Once the silicone gel has set, typically at an elevated temperature of approximately 160° C., the injection hole at location 134 is sealed in a seal step 256 using the same material as used for fabricating first shell 22, and the construction of the breast implant terminates (in an end step 258).

Breast implant 21 is depicted in FIG. 8 as having the cross-sectional shape of an oval. However, due to the flexibility of the material of first shell 22 and completed second shell 23, as well as the elasticity of filler material 132, it will adapt its shape according to the surrounding tissue as shown in FIG. 1.

According to the inventors' experiments, embodiments of the present invention reduce the weight of the implant by 30-35%, without affecting its tactile properties, by introducing a second sealed shell into the filler material within the first shell.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. An implantable device, comprising:
   a first sealed flexible shell configured for implantation within a breast of a human subject;
   an elastic filler material contained within the first sealed flexible shell;
   a second sealed flexible shell, which is disposed within the elastic filler material inside the first sealed flexible shell; and
   a volume of gas contained within the second sealed flexible shell, such that the volume of the gas is less than a threshold inflation volume required to induce a non-zero strain in the second sealed flexible shell when the device is subject to an external pressure of one atmosphere.

2. The implantable device according to claim 1, wherein the elastic filler material comprises silicone gel.

3. The implantable device according to claim 1, wherein the volume of gas comprises a volume of air.

4. The implantable device according to claim 1, wherein the volume of the gas comprises 85% of the threshold inflation volume.

5. A method for manufacturing an implantable device, the method comprising:
   providing a first sealed flexible shell configured for implantation within a breast of a human subject;
   filling the first sealed flexible shell with an elastic filler material;
   disposing a second sealed flexible shell within the elastic filler material inside the first sealed flexible shell; and
   inflating the second sealed flexible shell with a volume of gas, such that the volume of the gas is less than a threshold inflation volume required to induce a non-zero strain in the second sealed flexible shell when the device is subject to an external pressure of one atmosphere.

6. The method according to claim 5, wherein filling the first sealed flexible shell comprises filling it with silicone gel.

7. The method according to claim 5, wherein inflating the second sealed flexible shell comprises inflating it with air.

8. The method according to claim 5, wherein the volume of the gas comprises 85% of the threshold inflation volume.

* * * * *